US008825775B2

(12) United States Patent
Bohner et al.

(10) Patent No.: US 8,825,775 B2
(45) Date of Patent: Sep. 2, 2014

(54) METHODS AND APPARATUS TO CORRELATE HEALTHCARE INFORMATION

(75) Inventors: Wendy Lynne Bohner, Grayslake, IL (US); David P. Murawski, Cary, IL (US); Alan F. James, Salt Lake City, UT (US); Niranjan Kumar Sharma, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 13/031,385

(22) Filed: Feb. 21, 2011

(65) Prior Publication Data

US 2012/0215857 A1    Aug. 23, 2012

(51) Int. Cl.
G06F 15/16      (2006.01)

(52) U.S. Cl.
USPC .......................................................... 709/206

(58) Field of Classification Search
USPC ...................... 709/206, 203, 220; 715/223
See application file for complete search history.

(56) References Cited

U.S. PATENT DOCUMENTS

| 7,685,111 | B2 | 3/2010 | Muroi et al. | |
| 7,734,668 | B2 | 6/2010 | Aoki et al. | |
| 2004/0010425 | A1* | 1/2004 | Wilkes et al. | 705/3 |
| 2010/0017225 | A1* | 1/2010 | Oakley et al. | 705/2 |
| 2011/0218821 | A1* | 9/2011 | Walton et al. | 705/3 |

OTHER PUBLICATIONS

James A. Cimino, "Desiderata for Controlled Medical Vocabularies in the Twenty-First Century," Methods of Information in Medicine 37(4-5), pp. 394-403 (Nov. 1998).
Huff et al., "Development of the Logical Observation Identifier Names and Codes (LOINC) Vocabulary," Journal of the American Medical Informatics Association, vol. 5, No. 3, pp. 276-292 (1998).
Stan Huff, "LOINC (Logical Observation Identifier Names and Codes: Presentation to NCVHS)," May 17, 1999, retrieved at http://www.google.com/url?sa=t&rct=j&q=&esrc=s&source=web&cd=1& ved=0CCkQFjAA&url=http%3A%2F%2Fwww.ncvhs.hhs.gov%2F990517p6.ppt&ei=UMZAUsSwN4n52AXgroCgDg&usg=AFQjCNFPLPtx9hjvDpflr8x98c-8okOeAg on Sep. 23, 2013 (24 pages).
Stanley M. Huff, Roberto A. Rocha, Joseph F. Coyle and Scott P. Narus, "Integrating Detailed Clinical Models Into Application Development Tools," Studies in Health Technology and Informatics 107 Pt. 2, pp. 1058-1062 (2004).
Lee Min Lau and Stew Hong Lam, "Applying the Desiderata for Controlled Medical Vocabularies," Proceedings of the American Medical Informatics Association, pp. 97-101 (1999).

(Continued)

*Primary Examiner* — Vivek Srivastava
*Assistant Examiner* — Normin Abedin
(74) *Attorney, Agent, or Firm* — Hanley, Flight & Zimmerman, LLC

(57) ABSTRACT

Methods and apparatus to correlate healthcare information are disclosed. An example method includes receiving a healthcare message from a first entity of a healthcare enterprise, wherein the healthcare message is configured according to a first identification schema of the first entity; identifying one or more subjects of the healthcare message for correlation into an electronic clinical information system; selecting one of a plurality of correlators for each identified subject to correlate each identified subject, wherein each of the correlators are customizable to handle a specific type of healthcare message subject; and correlating the identified subjects of the message to associate each of the identified subjects with an identifier internal to the electronic clinical information system.

18 Claims, 5 Drawing Sheets

(56) References Cited

OTHER PUBLICATIONS

Lee Min Lau, Stew Hong Lam, Stanley M. Huff, "Comparing Encounter and Demographics Data Elements among Different Healthcare Enterprises Using a Common Data Disctionary," Proceedings of the American Medical Informatics Association, p. 1034 (1998).

Roberto De Almeida Rocha, Development and Evaluation of a Semantic Data Model for Chest Radiology, Department of Medical Informatics, University of Utah, 1996 (266 pages).

Roberto A. Rocha, Stanley M. Huff, "Using Digrams to Map Controlled Medical Vocabularies," Proceedings of the Annual Symposium on Computer Application in Medical Care, pp. 172-176 (1994).

\* cited by examiner

METHODS AND APPARATUS TO CORRELATE HEALTHCARE INFORMATION

FIELD OF THE DISCLOSURE

The present disclosure relates generally to healthcare information systems and, more particularly, to methods and apparatus to correlate healthcare information.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information, and/or scheduling information. Different healthcare entities may identify electronic records according to different policies or rules using different information and/or types of information.

SUMMARY

An example computer implemented method includes receiving a healthcare message from a first entity of a healthcare enterprise, wherein the healthcare message is configured according to a first identification schema of the first entity; identifying one or more subjects of the healthcare message for correlation into an electronic clinical information system; selecting one of a plurality of correlators for each identified subject to correlate each identified subject, wherein each of the correlators are customizable to handle a specific type of healthcare message subject; and correlating the identified subjects of the message to associate each of the identified subjects with an identifier internal to the electronic clinical information system.

An example tangible machine readable medium has instructions stored thereon that, when executed, cause a machine to at least receive a healthcare message from a first entity of a healthcare enterprise, wherein the healthcare message is configured according to a first identification schema of the first entity; identify one or more subjects of the healthcare message for correlation into an electronic clinical information system; select one of a plurality of correlators for each identified subject to correlate each identified subject, wherein each of the correlators are customizable to handle a specific type of healthcare message subject; and correlate the identified subjects of the message to associate each of the identified subjects with an identifier internal to the electronic clinical information system.

An example apparatus includes a data feed to receive a healthcare message from a first entity of a healthcare enterprise, wherein the healthcare message is configured according to an identification schema of the first entity; an identifier to identify one or more subjects of the healthcare message for correlation into an electronic clinical information system; and a selector to select one of a plurality of correlators for each identified subject to correlate each identified subject, wherein each of the correlators are customizable to handle a specific type of healthcare message subject, and wherein the correlators are to correlate the identified subjects of the message to associate each of the identified subjects with an identifier internal to the electronic clinical information system.

Figure 1:
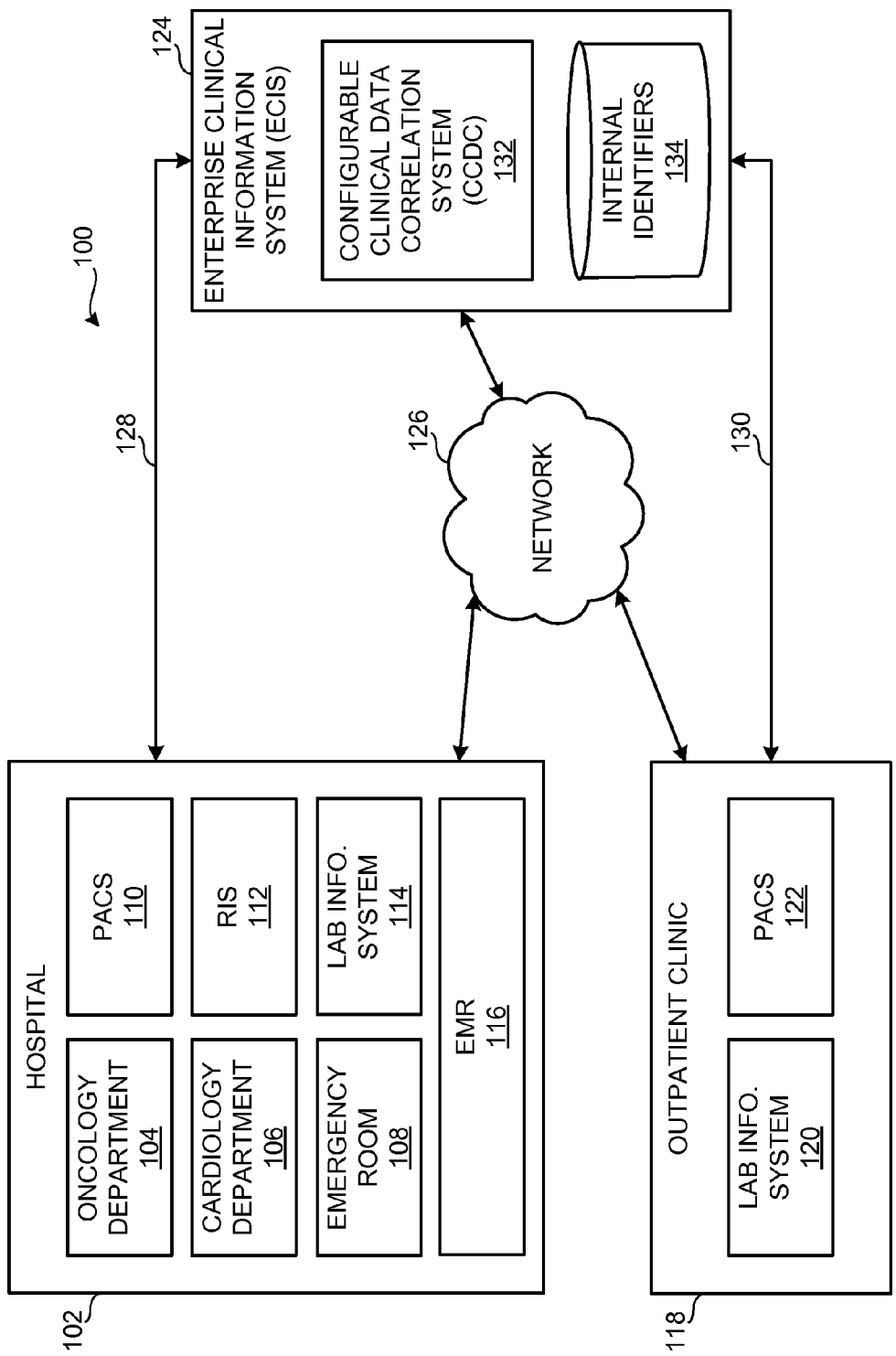
FIG. 1 is a block diagram of an example healthcare environment.

The foregoing summary, as well as the following detailed description of certain implementations of the methods, apparatus, systems, and/or articles of manufacture described herein, will be better understood when read in conjunction with the appended drawings. It should be understood, however, that the methods, apparatus, systems, and/or articles of manufacture described herein are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Generally, the example methods, apparatus, systems, and/or articles of manufacture disclosed herein correlate healthcare information from healthcare enterprise(s) for an enterprise clinical information system (ECIS). Among other functions and/or benefits, the example ECIS supports healthcare practitioners in decision making processes by aggregating healthcare information across disparate enterprises and/or entities thereof and referencing collection(s) of data (e.g., guidelines, recommendations related treatment and/or diagnosis, studies, histories, etc.) to automatically generate supportive information to be communicated to one or more healthcare practitioners related to the aggregated healthcare information.

As part of the aggregation process and/or other processes implemented by the example ECIS, the ECIS receives healthcare messages that vary with respect to the manner in which the subjects of the messages are identified. Even when different healthcare enterprises or entities use standardized messages (e.g., Health Level 7 messages), the manner in which each enterprise or entity utilizes the standard may vary. In other words, different healthcare entities use different information or identifiers to make a message unique to a certain subject, even when using standardized message formats. A subject may refer to a patient associated with the message, an encounter associated with the message, a provider associated with the message, a treatment location associated with the message, an observation associated with the message, an order associated with the message, and/or any other healthcare subject. For example, a first healthcare entity (e.g., an oncology department of a healthcare enterprise, such as the Mayo Clinic®) may use a first set of identifiers to make a healthcare message unique to a patient, while a second healthcare entity (e.g., a cardiology department of the Mayo Clinic®) may use a second, different set of identifiers to make a healthcare message unique to a patient. As an illustration, the first set of identifiers may include a patient identification number (PID), a PID assigning authority (i.e., the entity that assigned the PID to the patient), and a last name, while the second set of identifiers may include social security number (SSN) and a last name. Additionally or alternatively, the ECIS may handle healthcare messages from separate enterprises, which also may differ in the manner in which patients of message are made unique (e.g., by using different identifier(s) to identify a patient). In other words, the ECIS may receive differently formatted healthcare messages from different entities of a single healthcare enterprise and/or differently formatted healthcare message from different healthcare enterprises altogether.

The examples disclosed herein enable the ECIS to correlate a healthcare message received from a healthcare enterprise (e.g., a hospital, a clinic, a physician's office, etc.) into an internal identifier that the ECIS can use for a subject of the healthcare message across processing devices or systems of the ECIS. That is, subjects of incoming healthcare messages are correlated into internal identifiers that are unique to the subjects according to an identification schema internal to the ECIS. As a result, the ECIS is aware of relationships between healthcare messages having a common subject (e.g., patient or encounter) and can utilize the relationship information for one or more services provided by the ECIS. As described in greater detail below, the example correlators disclosed herein are configured such that a user of the ECIS can customize the correlation process depending on one or more factor(s), such as a type of the subject to be correlated. In addition to the type of the subject to be correlated, additional or alternative factors can be used to determine how one or more of the example correlators disclosed herein can be customized and/or how one or more of the example correlators disclosed herein are selected for correlating a received healthcare message. As described in detail below, the customization of the correlators can be implemented in algorithms or bundled plug-ins created by a user(s) of the ECIS that dictate how the customized correlator(s) are to correlate the subject of the received healthcare message into an internal identifier for the ECIS. The example methods, apparatus, systems, and/or articles of manufacture disclosed herein are described in greater detail below in connection with the figures.

FIG. 1 is a block diagram of an example healthcare environment 100 in which the example methods, apparatus, systems, and/or articles of manufacture disclosed herein to correlate healthcare information may be implemented. The example healthcare environment 100 of FIG. 1 includes a first hospital 102 having a plurality of entities operating within and/or in association with the first hospital 102. In the illustrated example, the entities of the first hospital 102 include an oncology department 104, a cardiology department 106, an emergency room system 108, a picture archiving and communication system (PACS) 110, a radiology information system (RIS) 112, and a laboratory information system (LIS) 114. The oncology department 104 includes cancer-related healthcare practitioners, staff and the devices or systems that support oncology practices and treatments. Similarly, the cardiology department 106 includes cardiology-related healthcare practitioners, staff and the devices and/or systems that support cardiology practices and treatments. Notably, the example oncology department 104 of FIG. 1 has specific, designated policies and protocols for the generation, reception, transmission and, more generally, processing of healthcare documentation. At the same time, the example cardiology department 106 of FIG. 1 has specific, designated policies and protocols for the generation, reception, transmission and, more generally, processing of healthcare documentation that differ from the policies and protocols of the example oncology department 104 of FIG. 1. For example, the oncology department 104 may use a first set of identifiers to make a subject of a Health Level 7 (HL7) Admit Discharge Transfer (ADT) message unique, while the cardiology department 106 uses a second set of identifiers different from the first set of identifiers to make a subject of a Healthcare Level 7 ADT message unique. Such differences may also exist between the emergency room 108, the PACS 110, the RIS 112 and/or the accounting services 114.

Briefly, the emergency room system 108 manages information related to the emergency care of patients presenting at an emergency room of the hospital 102, such as admission information, observations from emergency examinations of patients, treatments provided in the emergency room setting, etc. The PACS 110 stores medical images (e.g., x-rays, scans, three-dimensional renderings, etc.) as, for example, digital images in a database or registry. Images are stored in the PACS 110 by healthcare practitioners (e.g., imaging technicians, physicians, radiologists) after a medical imaging of a patient and/or are automatically transmitted from medical imaging devices to the PACS 110 for storage. The RIS 112 stores data related to radiology practices such as, for example, radiology reports, messages, warnings, alerts, patient scheduling information, patient demographic data, patient tracking information, and/or physician and patient status monitors, as well as enables exam order entry (e.g., ordering an x-ray of a patient) and image and film tracking (e.g., tracking identities of one or more people that have checked out a film). The lab information system 114 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-114, as the entities 104-114 and the information listed above is included herein as non-limiting examples. Further, the information stored in entities 104-114 may overlap and/or be combined into one or more of the entities 104-114. Each of the example entities 104-114 of FIG. 1 interacts with an electronic medical record (EMR) system 116. Generally, the EMR 116 stores electronic copies of healthcare records associated with, for example, the hospital 102 and the entities 104-114 thereof.

The example healthcare environment 100 of FIG. 1 also includes an outpatient clinic 118 as an example of another healthcare enterprise. The example outpatient clinic 118 of FIG. 1 includes a lab information system 120 and a PACS 122 that operate similarly to the corresponding entities of the example hospital 102. The lab information system 120 and the PACS 122 of the example outpatient clinic 118 generate and/or process healthcare messages differently as described above in connection with the hospital 102. Thus, differences in healthcare information processing exist between the entities of a healthcare enterprise and between healthcare enterprises in general.

In the illustrated example of FIG. 1, the hospital 102 and the outpatient clinic 118 are in communication with an ECIS 124 via a network 126, which may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the example hospital 102 and/or the example outpatient clinic 118 are in communication with the example ECIS 124 via direct or dedicated transmission mediums 128 and 130.

Generally, the ECIS 124 supports healthcare information processing implemented by systems, devices, applications, etc. of healthcare enterprises, such as the hospital 102 and the outpatient clinic 118. The ECIS 124 is capable of processing healthcare messages from different entities of healthcare enterprises (e.g., the entities 104-114 of the hospital 102) that may generate, process and/or transmit the healthcare messages differently and/or using different formats, protocols, policies, terminology, etc. when generating, processing, and/or transmitting the healthcare messages. Moreover, the example ECIS 124 of FIG. 1 supports healthcare practitioners in decision making processes by aggregating healthcare information across disparate enterprises and/or entities thereof and referencing collection(s) of data to automatically generate suggestive and/or definitive data for communication to one or more healthcare practitioners related to the aggregated healthcare information.

To enable the example ECIS 124 of FIG. 1 to perform these and/or additional services or functions, the example ECIS 124 includes a configurable clinical data correlation (CCDC) system 132 to correlate healthcare messages for use in the ECIS 124. Generally, the example CCDC system 132 of FIG. 1 includes a plurality of customizable correlators that receive data from incoming healthcare messages and correlate the received data such that subject(s) (e.g., patients, encounters, lab results, orders, locations, providers, observations, etc.) of the incoming healthcare messages can be associated with identifier(s) internal to the ECIS 124. That is, the example CCDC system 132 disclosed herein enables the ECIS 124 to process and/or utilize data from incoming healthcare messages using an internal identifier that can be tied to or associated with other information that has been associated with the internal identifier within the ECIS 124. The ECIS 124 may use such internal identifiers to, for example, gather information related to a particular subject, such as a patient, encounter, healthcare provider, etc. In the illustrated example of FIG. 1, the internal identifiers are stored in a database 134 associated with the ECIS 132.

Users of the ECIS 124, such as members of a service support team associated with the ECIS 124 or a customer interface support team, can create and customize the correlators of the CCDC system 132 based on, for example, a type of subject of a message to be associated with the internal identifier and/or a source of the message. For example, one or more of the correlators may be customized to perform an additional verification, for example, of an identify of a patient by checking certain fields of an incoming healthcare message in addition to external identifiers that the hospital 102 uses to make the healthcare message unique to a patient when the healthcare message is received from the laboratory information system 114. Such a customization may be put in place due to a tendency of the laboratory information system 114 to include insufficient identifying information in healthcare messages transmitted to the ECIS 124. The customizations disclosed herein can be implemented via, for example, a graphical interface tool provided by the ECIS 124 and/or a device or system associated with the ECIS 124 and/or the CCDC system 132. Additional or alternative customizations and aspects of the example CCDC system 132 are described below in connection with FIG. 2.

Figure 2:
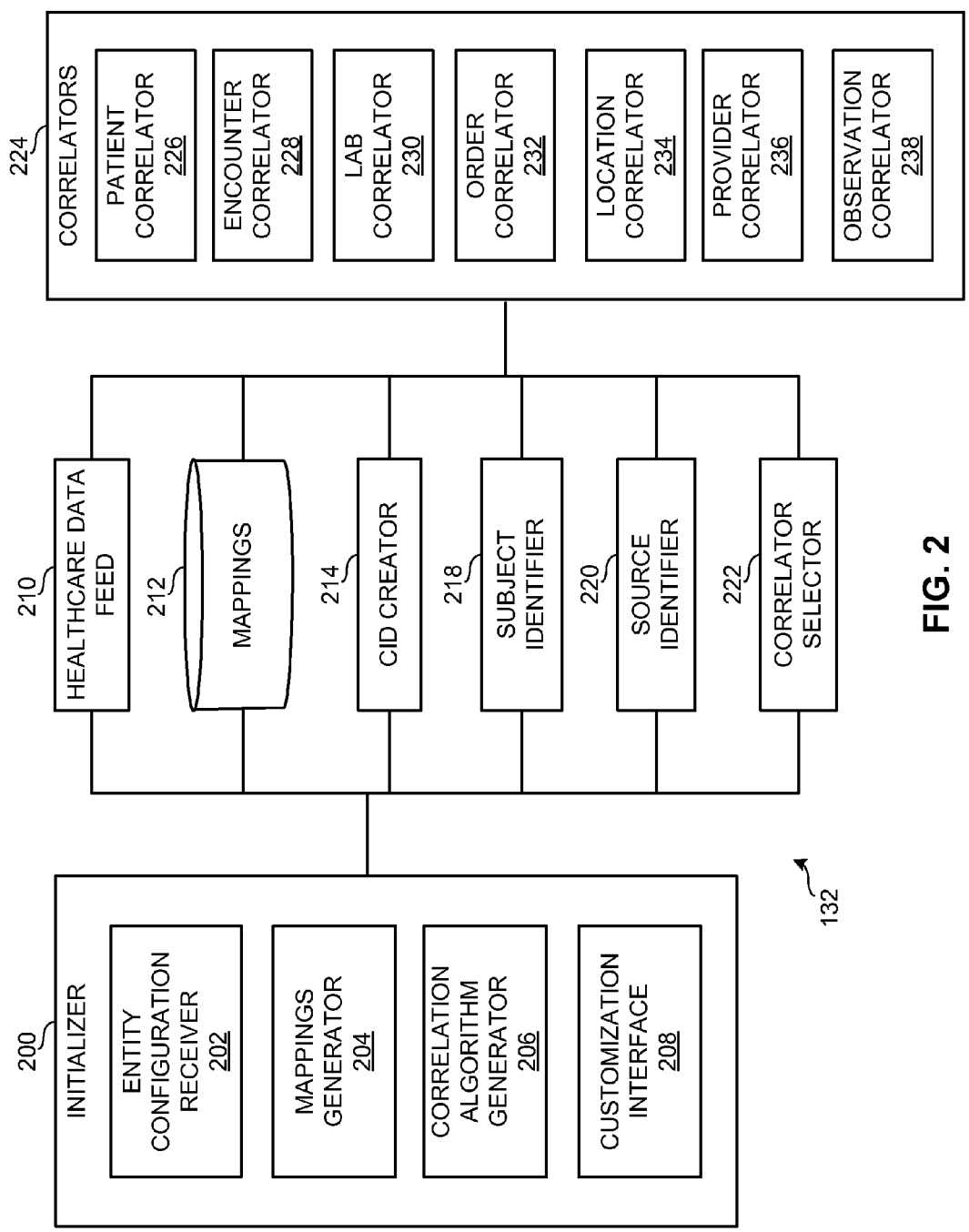
FIG. 2 is a block diagram of an example apparatus that may be used to implement the example configurable clinical data correlation (CCDC) system of FIG. 1.

FIG. 2 is a block diagram of an example apparatus that may be used to implement the example CCDC system 132 of FIG. 1. In the illustrated example of FIG. 2, the example CCDC system 132 includes an initializer 200 having an entity configuration receiver 202, a mapping generator 204, a correlation algorithm generator 206 and a customization interface 208. The example CCDC system 132 of FIG. 2 also includes a healthcare data feed 210, mappings 212, a clinical identifier creator 214, an object identifier 216 having a subject identifier 218 and a source identifier 220, a correlator selector 222 and a plurality of correlators 224. In the illustrated example of FIG. 2, the plurality of correlators 224 includes a patient correlator 226, an encounter correlator 228, a laboratory correlator 230, an order correlator 232, a location correlator 234, a provider correlator 236 and an observation correlator 238. While an example manner of implementing the CCDC system 132 of FIG. 1 has been illustrated in FIG. 2, one or more of the elements, processes and/or devices illustrated in FIG. 2 may be combined, divided, re-arranged, omitted, eliminated and/or implemented in any other way. Further, the example initializer 200, the example entity configuration receiver 202, the example mapping generator 204, the example correlation algorithm generator 206, the example customization interface 208, the example healthcare data feed 210, the example clinical identifier creator 214, the example object identifier 216, the example subject identifier 218, the example source identifier 220, the example correlator selector 222, the example patient correlator 226, the example encounter correlator 228, the example laboratory correlator 230, the example order correlator 232, the example location correlator 234, the example provider correlator 236, the example observation correlator 238, and/or, more generally, the example CCDC system 132 of FIG. 2 may be implemented by hardware, software, firmware and/or any combination of hardware, software and/or firmware. Thus, for example, any of the example initializer 200, the example entity configuration receiver 202, the example mapping generator 204, the example correlation algorithm generator 206, the example customization interface 208, the example healthcare data feed 210, the example clinical identifier creator 214, the example object identifier 216, the example subject identifier 218, the example source identifier 220, the example correlator selector 222, the example patient correlator 226, the example encounter correlator 228, the example laboratory correlator 230, the example order correlator 232, the example location correlator 234, the example provider correlator 236, the example observation correlator 238, and/or, more generally, the example CCDC system 132 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the example initializer 200, the example entity configuration receiver 202, the example mapping generator 204, the example correlation algorithm generator 206, the example customization interface 208, the example healthcare data feed 210, the example clinical identifier creator 214, the example object identifier 216, the example subject identifier 218, the example source identifier 220, the example correlator selector 222, the example patient correlator 226, the example encounter correlator 228, the example laboratory correlator 230, the example order correlator 232, the example location correlator 234, the example provider correlator 236, the example observation correlator 238, and/or, more generally, the example CCDC system 132 of FIG. 2 are hereby expressly defined to include a tangible medium such as a memory, DVD, CD, etc., storing the software and/or firmware. Further still, the example CCDC system 132 of FIG. 2 may include one or more elements, processes and/or devices in addition to, or instead of, those illustrated in FIG. 2, and/or may include more than one of any or all of the illustrated elements, processes and devices.

The example initializer 200 is utilized by, for example, a programmer associated with the ECIS 124 when a healthcare enterprise, such as the hospital 102, incorporates or registers with the ECIS 124. Additionally, the example initializer 200 of FIG. 2 is utilized when a healthcare enterprise already registered with or incorporated into the ECIS 124 undergoes a change or update that alters, for example, the mappings 212 (which are described in detail below). When the initializer 200 is triggered by, for example, the hospital 102 registering with the ECIS 124, the entity configuration receiver 202 obtains or receives information related to the policies, protocols, terminology, etc. used by each entity of the hospital 102 in association with healthcare documentation procedures. That is, the example entity configuration receiver 202 of FIG. 2 determines the schema or manner in which each entity of the hospital 102 makes healthcare messages unique to the subjects of the healthcare messages. For example, the configuration receiver 202 may determine that the oncology department 104 of the hospital 102 uses (1) a social security number, (2) a patient last name and (3) a primary healthcare provider to make a healthcare message unique to a patient that is the subject of the healthcare message. In some examples, the entity configuration receiver 202 may determine that the oncology department 104 of the hospital 102 uses (1) a patient last name, (2) a date of occurrence and (3) a location of treatment to make a healthcare message unique to an encounter that is the subject of the healthcare message. In some examples, the entity configuration receiver 202 may determine that the cardiology department 106 of the hospital uses (1) a patient identification number, (2) the assigning authority that assigned the patient identification number and (3) a date of birth to make a healthcare message unique to a patient that is the subject of the healthcare message. Thus, the entity configuration receiver 202 may determine that the same entity has different protocols or methods of identifying different subjects of messages and/or that different entities have different protocols or methods of identifying the same type of subjects of messages. As a result of the findings of the entity configuration receiver 202, the CCDC system 134 is aware of sets of external identifiers or schema used by different entities to make subjects of healthcare message unique.

The findings of the entity configuration receiver 202 are conveyed to the example mappings generator 204. The example mappings generator 204 creates schema to schema mappings capable of mapping the information of the incoming healthcare message into a clinical identifier (CID) to be used by one of the correlators 224 as described below. The schema to schema mappings are stored in the example mappings 212 in FIG. 2 as, for example, Estensible Stylesheet Language (XSL) files. To continue the above example, when the entity configuration receiver 202 obtains the schema by which the oncology department 104 of the hospital 102 makes a healthcare message unique to a patient, that schema can be mapped to a schema of the CID to be used by the patient correlator 226. As a result the three example identifiers listed above that embody the patient message schema of the oncology department 104 are mapped to the schema for the corresponding CID using the mappings 212 generated by the mapping generator 204.

The example correlation algorithm generator 206 enables a user, such as a programmer associated with the ECIS 124, to create one or more plug-in bundles to implement the correlators 224 described herein. Generally, and as described in detail below in connection with the correlators 224, the correlation algorithms generated by the generator 206 are configured to use a corresponding CID (into which the external identifiers of an incoming healthcare message are mapped) to correlate the subject of the healthcare message with an identifier internal to the ECIS 124. The example correlation algorithm generator 206 works in conjunction with the customization interface 208 to enable the user of the ECIS 124 to generate custom algorithms for that correlation and/or the alter an existing algorithm as the user sees fit. The customization interface 208 may be implemented by any suitable user interface that, for example, provides the capability to write and/or implement one or more scripts using any suitable scripting protocol or language. In some examples, the customization interface 208 provides the user with a plurality of pre-defined options or actions that the user can choose from to add to a customized workflow of the correlation algorithms.

In the illustrated example, the correlation algorithm generator 206 generates different correlators 224 based on a type of the subject of the healthcare message to be correlated into the ECIS 124. As illustrated in FIG. 2, the correlators 224 include the patient correlator 226 for instances in which the incoming healthcare message has a patient as the subject or when patient information of the healthcare message is desired to be correlated into the ECIS 124 (e.g., according to a field received with the healthcare message or a field mapped into the corresponding CID using the mappings 212), the encounter correlator 228 for instances in which the incoming healthcare message has an encounter as the subject or when encounter information of the healthcare message is desired to be correlated into the ECIS 124, the laboratory correlator 230 for instances in which the incoming healthcare message has a lab report or result as the subject or when laboratory information of the healthcare message is desired to be correlated into the ECIS 124 (e.g., according to a field received with the healthcare message or a field mapped into the corresponding CID using the mappings 212), the order correlator 232 for instances in which the incoming healthcare message has an order as the subject or when order information of the healthcare message is desired to be correlated into the ECIS 124 (e.g., according to a field received with the healthcare message or a field mapped into the corresponding CID using the mappings 212), the location correlator 234 for instances in which the incoming healthcare message has a location of an aspect of treatment as the subject or when location information of the healthcare message is desired to be correlated into the ECIS 124 (e.g., according to a field received with the healthcare message or a field mapped into the corresponding CID using the mappings 212), the provider correlator 236 for instances in which the incoming healthcare message has a healthcare provider as the subject or when provider information of the healthcare message is desired to be correlated into the ECIS 124 (e.g., according to a field received with the healthcare message or a field mapped into the corresponding CID using the mappings 212), the observation correlator 238 for instances in which the incoming healthcare message has a clinical observation as the subject or when observation information of the healthcare message is desired to be correlated into the ECIS 124 (e.g., according to a field received with the healthcare message or a field mapped into the corresponding CID using the mappings 212). Moreover, the user or programmer using the customization interface 208 and the correlation algorithm generator 206 may customize the one or more of the correlators 224 based on a source of the incoming healthcare message, which may be placed into the corresponding CID when the message is mapping into the CID (e.g., by the CID creator 214). For example, the correlation algorithm generator 206 and the customization interface 208 can be used to cause a correlator to take additional or alternative steps or actions based on which entity of the hospital 102 from which the message was received.

After the initialization described above for at least one healthcare enterprise (e.g., the hospital 102 of FIG. 1), the healthcare data feed 210 of the example CCDC system 132 of FIG. 2 awaits and/or actively retrieves healthcare messages from one or more of the entities registered with the ECIS (e.g., the entities 104-114 of the hospital 102). The healthcare data feed 210 can be implemented by any suitable communication interface capable of facilitating communication between, for example, the hospital 102 and the ECIS 124. When a healthcare message is received at the data feed 210, the message is conveyed to the example source identifier 220. In the illustrated example, the source identifier 220 identifies a source of the received message based on, for example, a field of the message and/or data conveyed in association with the message to the ECIS 124. In the illustrated example, the source of the message is used by the CID creator 214 to reference or query the mappings 212. As described above, the mappings 212 include schema to schema indicators that inform the CID creator 214 of how the data of the message should be mapped into a CID. The CID creator 214 uses that information to pull data from the received message and to incorporate the pulled data in a CID according to the mappings 212. Thus, the CID created by the CID creator 214 includes data from the healthcare message formatted according to the internal schema of the ECIS 124. In addition, the CID creator 214 includes the external identifiers as received at the data feed 210 in the resulting CID.

The CID creator 214 also uses information obtained by the subject identifier 218, which identifies one or more subjects of the received message to be correlated. The CID creator 214 creates a CID for each of the identified subjects. As described above, each of the correlators 224 have a corresponding type of CID to be generated thereof. Thus, when the subject identifier 218 identifies a patient as a first subject from the received message to be correlated by the CCDC system 132, the CID creator 214 generates a first CID corresponding to the patient correlator 226. When the subject identifier 218 identifies an encounter as a second subject from the received message to be correlated by the CCDC system 132, the CID creator 214 generates a second CID corresponding to the encounter correlator 228. This is also the case for the remaining example correlators 230-238 of FIG. 2 and any other customized correlators implemented by the CCDC system 132.

Based on which type(s) of CID(s) were generated by the CID creator 214, the example correlator selector 222 selects one or more of the correlators 224. As a result, any CID that was created with a patient as the subject of the message to be correlated is passed to the patient correlator 226 according to the correlator selector 222. Similarly, any CID that was created with an encounter as the subject of the message to be correlated is passed to the encounter correlator 230 according to the correlator selector 222.

The selected one or more correlators 224 each receive a corresponding CID created by the CID creator 214. As described above, each of the correlators 224 includes one or more algorithms (e.g., plug-in bundles) that were generated and customized based on, for example, the subject of a healthcare message to be correlated into an internal identifier. Thus, the correlators 224 are each configured to determine which internal identifier of the ECIS 124 the respective subject (e.g., patient) of the incoming message is to be assigned or, if one already exists, associated with. To do so, the example correlators 224 reference one or more databases or data services, such as the internal identifiers database 136 of FIG. 1 to determine which existing internal identifier to which the received healthcare message is assigned or, when no such internal identifier exists, to generate a new internal identifier for the subject of the received healthcare message. Thus, the selected one(s) of the correlators 224 associates the incoming healthcare message with the appropriate (or new) internal identifier and stores the data in the internal identifier 136 database. Further, the selected one(s) of the correlators 224 may perform additional tasks or actions depending on the customization by the user of the ECIS 124 using the customization interface 208. Illustrative examples of the functionality of the example CCDC system 132 of FIG. 2 are described below in connection with FIGS. 3 and 4.

Figure 3:
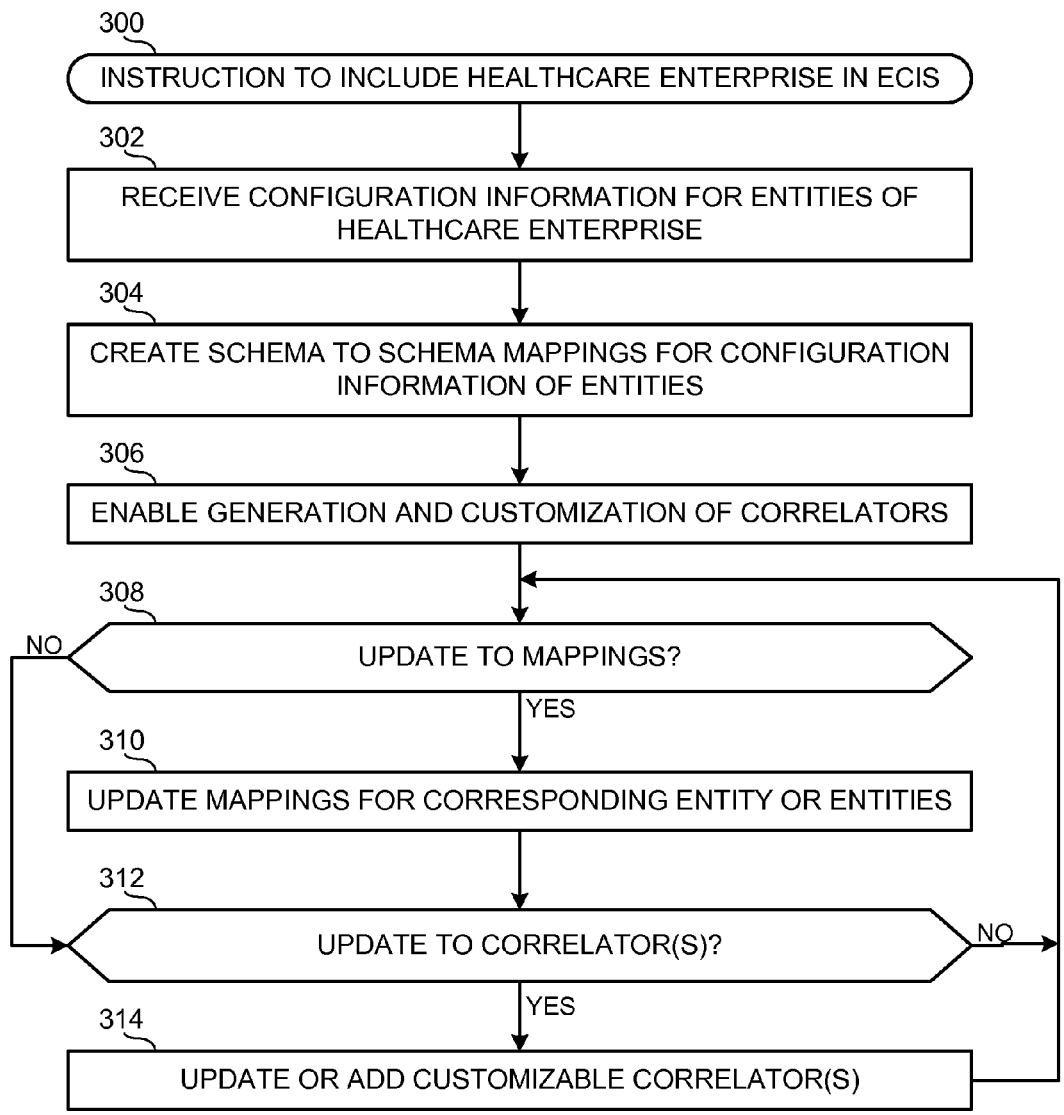
FIG. 3 is a flow diagram representative of example machine readable instructions that may be executed to implement the example CCDC system of FIGS. 1 and/or 2.
Figure 4:
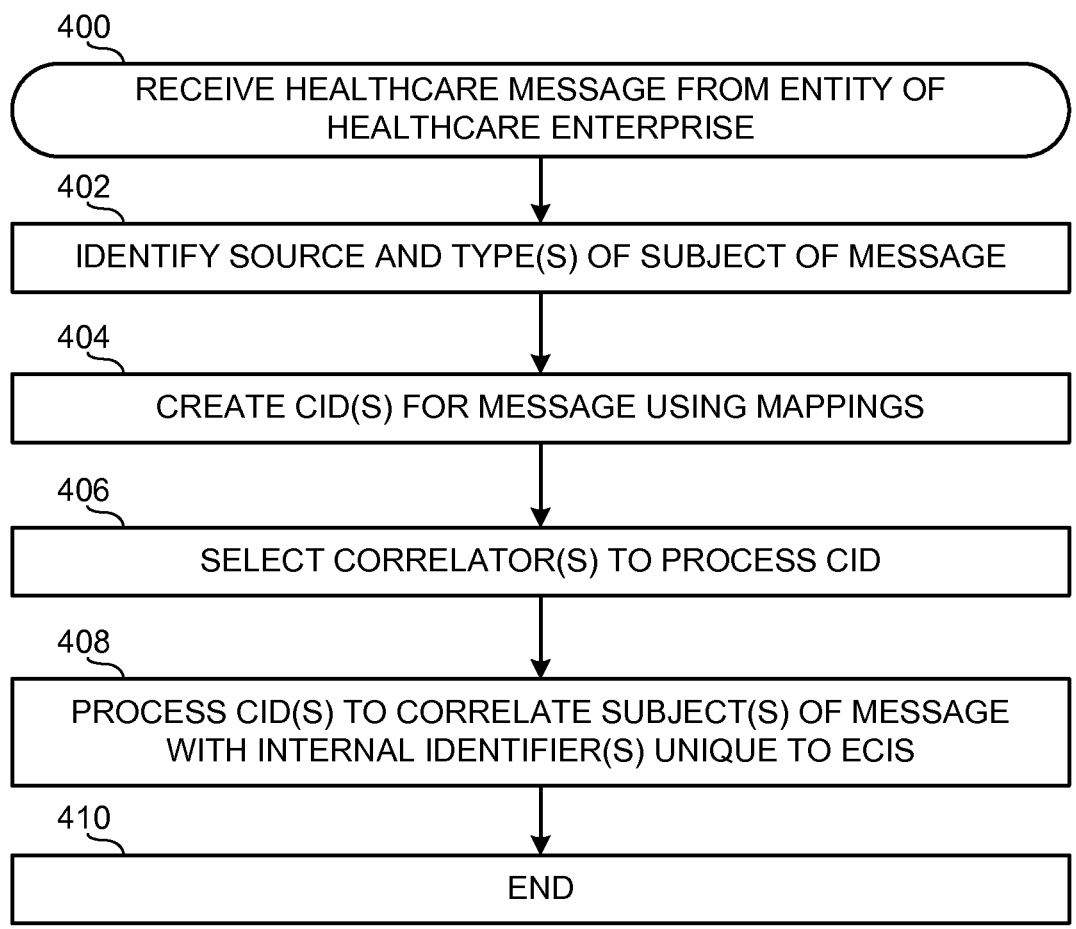
FIG. 4 is a flow diagram representative of example machine readable instructions that may be executed to implement the example CCDC system of FIGS. 1 and/or 2.

The flow diagrams depicted in FIGS. 3 and 4 are representative of machine readable instructions that can be executed to implement the example CCDC system 132 of FIGS. 1 and/or 2 to correlate healthcare information. The example processes of FIGS. 3 and 4 may be performed using a processor, a controller and/or any other suitable processing device. For example, the example processes of FIGS. 3 and 4 may be implemented in coded instructions stored on a tangible medium such as a flash memory, a read-only memory (ROM) and/or random-access memory (RAM) associated with a processor (e.g., the example processor 512 discussed below in connection with FIG. 5). Alternatively, some or all of the example processes of FIGS. 3 and 4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3 and 4 may be implemented manually or as any combination(s) of any of the foregoing techniques, for example, any combination of firmware, software, discrete logic and/or hardware. Further, although the example processes of FIGS. 3 and 4 are described with reference to the flow diagrams of FIGS. 3 and 4, other methods of implementing the processes of FIGS. 3 and 4 may be employed. For example, the order of execution of the blocks may be changed, and/or some of the blocks described may be changed, eliminated, sub-divided, or combined. Additionally, any or all of the example processes of FIGS. 3 and 4 may be performed sequentially and/or in parallel by, for example, separate processing threads, processors, devices, discrete logic, circuits, etc.

Turning to FIG. 3, when the hospital 102 of FIG. 1 registers with or updates a registration with the ECIS 124 of FIG. 1 (block 300), the initializer 200 of FIG. 2 triggers the entity configuration receiver 202 to obtain information related to the policies, protocols, formats, terminology, etc. of each entity 104-114 of the hospital 102 or one or more of the entities 104-114 being updated (block 302). For example, the emergency room system 108 may identify patients according to a first set of identifiers and encounters according to a second set of identifiers. Further, the laboratory information system 114 may identify patients according to a third set of identifiers and lab results according to a fourth set of identifiers. The example entity configuration receiver 202 obtains this information and, therefore, the example CCDC system of FIG. 2 is aware of the identifiers used by each entity of the hospital 102 to identify different types of subjects of healthcare messages (e.g., patient, encounters, lab results, orders, locations of treatment, healthcare provider, observation, etc.).

The entity configuration receiver 202 conveys the information regarding the entities 104-114 of the hospital 102 to the mappings generator 204 of FIG. 2 such that the mappings generator 204 can generate schema to schema mappings based on the configurations of the entities 104-114 (block 304). The schema to schema mappings generated by the mappings generator 204 enable different identification schema (e.g., the sets of identifiers used by each entity to identify subjects of healthcare messages) of different healthcare entities to be received and processed by the CCDC system 132 into a schema for use in the CIDs of the ECIS 124.

As a further initialization of the CCDC system 132 with respect to the hospital 102, the correlation algorithm generator 206 works in conjunction with the customization interface 208 to enable generation and customization of the correlators (block 306). The customization interface 208 may provide a programmer, for example, with a set of tools or interface to assist in the generator of custom algorithms embodied in scripts and/or plug-in bundles that define the correlators 224. A user of the ECIS 124 may customize the correlators based on, for example, a type of subject of received healthcare messages to be correlated into internal identifiers of the ECIS 124. Customization of the correlators 224 can be based on additional or alternative factor(s), such as the source of received healthcare messages or past experiences with the source of received healthcare messages that warrant unique treatment of the messages for the correlation process(es) described herein. The different customizations to the correlators are discussed above and in greater detail below in connection with FIG. 4.

The example flow diagram of FIG. 3 also includes checks to determine whether one or more updates are desired or required for the mappings 212 generated by the mappings generator 204 or the correlators 224 generated by the correlation algorithm generator 206. In particular, when an update occurs to one or more of the mappings 212 (block 308), such an update(s) is implemented at block 310. Similarly, if one or more updates occurs to the correlator(s) (block 312), such an update(s) is implemented at block 314. Other types of updates or changes can be implemented in addition to those illustrated in the example flow diagram of FIG. 3.

Turning to FIG. 4, a healthcare message is received at the healthcare data feed 210 of FIG. 2 (block 400). The healthcare message may be received at the data feed 210 as a result of, for example, the message being stored in the example EMR 116 of the hospital 102 and/or the message being directly transmitted to the ECIS 124 as part of a workflow of the ECIS 124. The received healthcare message may correspond to, for example, a lab report generated in association with the example laboratory information system 114 of FIG. 1. To continue the above example, according to the schema employed by the example laboratory information system 114 of FIG. 1 (as learned by the entity configuration receiver 202 at block 302 of FIG. 3) identifies patients according to a third set of identifiers and lab results according to a fourth set of identifiers, as opposed to the first and second sets of identifiers used by the emergency room system 108 for patients and encounters, respectively.

The received message also indicates that two subjects are to be correlated with an internal identifier of the ECIS 124, the two subjects being a patient and a lab result. The subject identifier 218 of FIG. 2 identifies those subjects as being those to be correlated and the source identifier 220 of FIG. 2 identifies the laboratory information system 114 as the source of the message (block 402). The source of the message is used to determine which of the mappings 212 to use to map the data of the message into a CID and the identified subjects are used to choose the CID(s) to create. The CID creator 214 then creates CID(s) for the received message, which includes pulling data, such as the identifiers of the third and fourth sets of identifiers used by the laboratory information system 114 from the message and incorporating the same into the CID(s) (block 404). To continue the above example, the CID creator 214 generates a first CID for the patient information of the received message and a second CID for the lab result information of the received message.

The example correlator selector 222, which is also aware of the subjects of the message to be correlated, selects the appropriate one(s) of the correlators 224 for correlation of the message (block 406). In the illustrated example, the selection of the correlator by the correlator selector 222 also includes conveyance of the corresponding CIDs to the selected correlators. Thus, to continue the above example, the correlator selector 222 selects the patient correlator 226 for the first CID created by the CID creator 214 for the patient data of the received message and conveys the first CID to the patient correlator 226. Additionally, the correlator selector 222 selects the lab correlator 230 for the second CID created by the CID creator 214 for the lab result data of the received message and conveys the second CID to the lab correlator 230. The selected correlators 226 and 230 then process the respective CIDs to correlate the corresponding subjects of the received message with respective internal identifiers for the ECIS 124 and stores the internal identifiers in the database 134 of FIG. 1 (block 408). As a result, the patient correlator 226 has associated patient data of the message received at the healthcare data feed 210 with an internal identifier than can be used uniformly across devices, programs and systems of the ECIS 124 to refer to the patient of the received message. Further, the lab correlator 230 has associated lab result data of the message received at the healthcare data feed 210 with an internal identifier than can be used uniformly across devices, programs and systems of the ECIS 124 to refer to the lab result of the received message. The other correlators 228 and 232-238, as well as additional customized correlators of the CCDC system 132 are capable of correlating different subjects of received messages in a similar fashion. The example of FIG. 4. ends (block 410).

Figure 5:
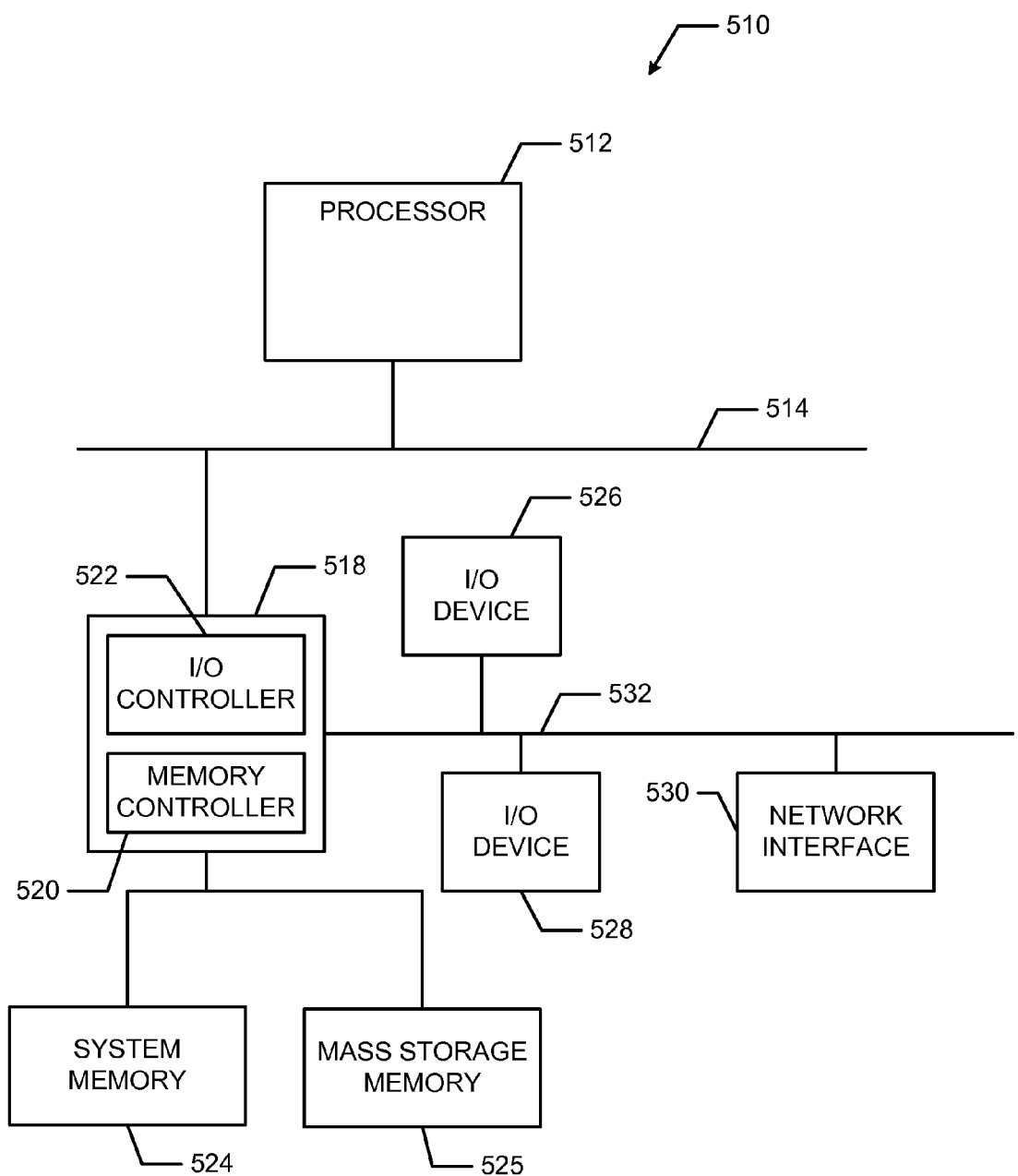
FIG. 5 is a block diagram of an example processor system that may be used to execute the machine readable instructions of FIGS. 3 and/or 4 to implement the example CCDC system of FIGS. 1 and/or 2.

FIG. 5 is a block diagram of an example processor system 510 that may be used to implement the apparatus and methods described herein. As shown in FIG. 5, the processor system 510 includes a processor 512 that is coupled to an interconnection bus 514. The processor 512 may be any suitable processor, processing unit or microprocessor. Although not shown in FIG. 5, the system 510 may be a multi-processor system and, thus, may include one or more additional processors that are identical or similar to the processor 512 and that are communicatively coupled to the interconnection bus 514.

The processor 512 of FIG. 5 is coupled to a chipset 518, which includes a memory controller 520 and an input/output (I/O) controller 522. As is well known, a chipset typically provides I/O and memory management functions as well as a plurality of general purpose and/or special purpose registers, timers, etc. that are accessible or used by one or more processors coupled to the chipset 518. The memory controller 520 performs functions that enable the processor 512 (or processors if there are multiple processors) to access a system memory 524 and a mass storage memory 525.

The system memory 524 may include any desired type of volatile and/or non-volatile memory such as, for example, static random access memory (SRAM), dynamic random access memory (DRAM), flash memory, read-only memory (ROM), etc. The mass storage memory 525 may include any desired type of mass storage device including hard disk drives, optical drives, tape storage devices, etc.

The I/O controller 522 performs functions that enable the processor 512 to communicate with peripheral input/output (I/O) devices 526 and 528 and a network interface 530 via an I/O bus 532. The I/O devices 526 and 528 may be any desired type of I/O device such as, for example, a keyboard, a video display or monitor, a mouse, etc. The network interface 530 may be, for example, an Ethernet device, an asynchronous transfer mode (ATM) device, an 802.11 device, a DSL modem, a cable modem, a cellular modem, etc. that enables the processor system 510 to communicate with another processor system.

While the memory controller 520 and the I/O controller 522 are depicted in FIG. 5 as separate blocks within the chipset 518, the functions performed by these blocks may be integrated within a single semiconductor circuit or may be implemented using two or more separate integrated circuits.

Thus, the example methods, apparatus, systems, and/or articles of manufacture disclosed herein enable an exchange of linkage information between healthcare entities such that healthcare practitioners associated with entities are quickly, efficiently, and accurately made aware of clinical items associated with medical issues of transferred patients. In addition to other benefits and advantages, the example methods, apparatus, systems, and/or articles of manufacture disclosed herein reduce or, in some instances, eliminate the need for the practitioners to reconcile clinical items with medical issues. As a result, the practitioners can provide more accurate and safe care in a more efficient manner. Additionally, the practitioners can focus a transfer process and the exchange of information associated therewith on the clinical items related to the medical issue(s) for which the patient is being transferred.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A computer implemented method, comprising:
   determining, at a configuration receiver, a first set of identifiers used by a first healthcare entity to uniquely identify subjects of healthcare messages and a second set of identifiers used by a second healthcare entity to uniquely identify subjects of healthcare messages by receiving information from the first and second healthcare entities, the first and second set of identifiers being different;
   generating, at a correlation generator, a plurality of correlators based on the first and second set of identifiers, the correlators to correlate subjects of incoming messages to the first and second set of identifiers,
   wherein each of the correlators is customizable to handle a specific type of healthcare message;
   storing the first and second sets of identifiers into an electronic clinical information system;
   in response to receiving a healthcare message from the first or second healthcare entity, identifying first one or more subjects of the healthcare message for correlation to an identifier stored in the electronic clinical information system;
   selecting, at a correlator selector, one of the correlators for each identified subject to correlate each identified subject; and
   correlating the identified subjects of the message using the selected correlator for each identified subject to associate each of the identified subjects with an identifier stored in the electronic clinical information system.

2. A computer implemented method as defined in claim 1, further comprising generating a first mapping of a first identification schema of the first healthcare entity to a second identification schema of the electronic clinical information system before the receiving of the healthcare message.

3. A computer implemented method as defined in claim 2, further comprising generating a second mapping of a third identification schema of the second healthcare entity different from the first identification schema to the second identification schema of the electronic clinical information system before the receiving of the healthcare message.

4. A computer implemented method as defined in claim 3, further comprising identifying a source of the healthcare message and selecting one of the first and second sets of identifiers based on the identified source for the correlation process.

5. A computer implemented method as defined in claim 1, wherein the first one or more subjects comprise at least one of a patient, an encounter, a laboratory report, an order, a location of treatment, a healthcare provider, or an observation.

6. A computer implemented method as defined in claim 1, wherein the correlators being customizable enables a user of the electronic clinical information system to implement actions in addition to the correlation process to be performed by the one or more correlators.

7. A tangible computer readable storage medium having instructions stored thereon that, when executed, cause a machine to at least:
　determine, at a configuration receiver, a first set of identifiers used by a first healthcare entity to uniquely identify subjects of healthcare messages and a second set of identifiers used by a second healthcare entity to uniquely identify subjects of healthcare messages, the first and second set of identifiers being different;
　generate, at a correlation generator, a plurality of correlators based on the identifiers, the correlators to correlate subjects of incoming messages to the first and second set of identifiers, wherein each of the correlators is customizable to handle a specific type of healthcare message;
　store the first and second sets of identifiers into an electronic clinical information system;
　in response to receiving a healthcare message from the first healthcare entity, identify first one or more subjects of the healthcare message corresponding to the first set of identifiers for correlation to an identifier stored in the electronic clinical information system;
　select, at a correlator selector, one of the correlators for each identified subject to correlate each identified subject; and
　correlate, using the selected correlator for each identified subject, the identified subjects of the message to associate each of the identified subjects with an identifier stored in the electronic clinical information system.

8. A tangible computer readable medium as defined in claim 7, wherein the instructions, when executed, cause a machine to generate a first mapping of a first identification schema of the first healthcare entity to a second identification schema of the electronic clinical information system before the receiving of the healthcare message.

9. A tangible computer readable medium as defined in claim 8, wherein the instructions, when executed, cause a machine to generate a second mapping of a third identification schema of the second healthcare entity different from the first identification schema to the second identification schema of the electronic clinical information system before the receiving of the healthcare message.

10. A tangible computer readable medium as defined in claim 9, wherein the instructions, when executed, cause a machine to identify a source of the healthcare message and select one of the first and second sets of identifiers based on the identified source for the correlation process.

11. A tangible computer readable medium as defined in claim 7, wherein the first one or more subjects comprise at least one of a patient, an encounter, a laboratory report, an order, a location of treatment, a healthcare provider, or an observation.

12. A tangible computer readable medium as defined in claim 7, wherein the correlators being customizable enables a user of the electronic clinical information system to implement actions in addition to the correlation process to be performed by the one or more correlators.

13. An apparatus, comprising:
　a configuration receiver to determine a first set of identifiers used by a first healthcare entity to uniquely identify subjects of healthcare messages and a second set of identifiers used by a second healthcare entity to uniquely identify subjects of healthcare messages, the first and second set of identifiers being different
　a data feed to receive a healthcare message;
　a correlation generator to generate a plurality of correlators based on the first set of identifiers and the second set of identifiers, wherein the correlators are customizable to handle a specific type of healthcare message;
　a database to store the first and second identifiers in an electronic clinical information system;
　an identifier to:
　　identify first one or more subjects of the healthcare message corresponding to the first set of identifiers when the received healthcare message is from the first healthcare entity for correlation to a corresponding identifier stored in the electronic clinical information system; and
　　identify second one or more subjects of the healthcare message corresponding to the second set of identifiers when the received healthcare message is from the second healthcare entity; and
　a selector to select one of the correlators for each identified subject to correlate each identified subject, wherein the correlators are to use the selected correlator for each identified subject to correlate the identified subjects of the message to associate each of the identified subjects with an identifier stored in the electronic clinical information system, wherein at least one of the identifier or the selector is implemented via a processor.

14. An apparatus as defined in claim 13, further comprising a generator to generate a first mapping of a first identification schema of the first entity to a second identification schema of the electronic clinical information system before the receiving of the healthcare message.

15. An apparatus as defined in claim 14, further comprising a generator to generate a third mapping of a second identification schema of the second healthcare entity different from the first identification schema to the second identification schema of the electronic clinical information system before the receiving of the healthcare message.

16. An apparatus as defined in claim 15, further comprising a source identifier to identify a source of the healthcare message.

17. An apparatus as defined in claim 13, wherein the first one or more subjects comprise at least one of a patient, an encounter, a laboratory report, an order, a location of treatment, a healthcare provider, or an observation.

18. An apparatus as defined in claim 13, wherein the correlators being customizable enables a user of the electronic clinical information system to implement actions in addition to the correlation process to be performed by the one or more correlators.

* * * * *